United States Patent
Nakayama et al.

(10) Patent No.: US 7,826,586 B2
(45) Date of Patent: Nov. 2, 2010

(54) X-RAY CT DEVICE AND METHOD OF IMAGING USING THE SAME

(75) Inventors: Tadahiro Nakayama, Yokohama (JP); Kazunobu Nagai, Yokohama (JP); Akiyuki Yokoyama, Yokohama (JP); Isamu Nitta, Yokohama (JP); Masato Nagata, Kawasaki (JP); Toyomasa Honda, Otawara (JP); Hidetoshi Kudo, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 55 days.

(21) Appl. No.: 12/200,240

(22) Filed: Aug. 28, 2008

(65) Prior Publication Data
US 2009/0060123 A1 Mar. 5, 2009

(30) Foreign Application Priority Data
Aug. 29, 2007 (JP) ............................. 2007-222722

(51) Int. Cl.
*H05G 1/00* (2006.01)
*H05G 1/10* (2006.01)
(52) U.S. Cl. ....................................... 378/15; 378/101
(58) Field of Classification Search ................... 378/4, 378/15, 19, 101–107
See application file for complete search history.

(56) References Cited

U.S. PATENT DOCUMENTS

| 5,608,771 | A  | * | 3/1997 | Steigerwald et al. | .......... 378/15 |
| 6,674,836 | B2 | * | 1/2004 | Harada et al. | ................ 378/107 |
| 7,197,113 | B1 | * | 3/2007 | Katcha et al. | ................ 378/101 |
| 2006/0165220 | A1 | * | 7/2006 | Takahashi et al. | ........... 378/109 |

FOREIGN PATENT DOCUMENTS

JP 3827335 7/2006

* cited by examiner

*Primary Examiner*—Irakli Kiknadze
(74) *Attorney, Agent, or Firm*—Oblon, Spivak, McClelland, Maier & Neustadt, L.L.P.

(57) ABSTRACT

An X-ray CT device including a stationary part; a rotary part rotatable relative to the stationary part; an X-ray tube provided at the rotary part for radiating X-ray beams on an object; an X-ray detector provided at the rotary part opposing the X-ray tube, and that detects the X-ray beams passed through the object; an image processor that generates cross-sectional images of the object based on a detection signal outputted from the X-ray detector; a display that shows the cross-sectional images based on output signals delivered from the image processor; a first transmitting section configured by a rotary step-up transformer having a primary and secondary windings residing at the stationary and the rotary part respectively, and that steps up AC voltage provided by AC power source, and that further executes non-contact power transmission from the stationary part to the rotary part for supplying power to the X-ray tube.

19 Claims, 10 Drawing Sheets

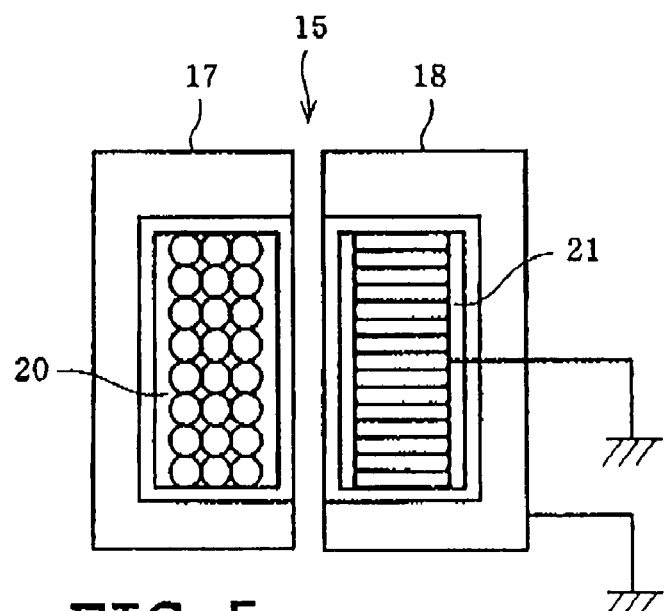
FIG. 5
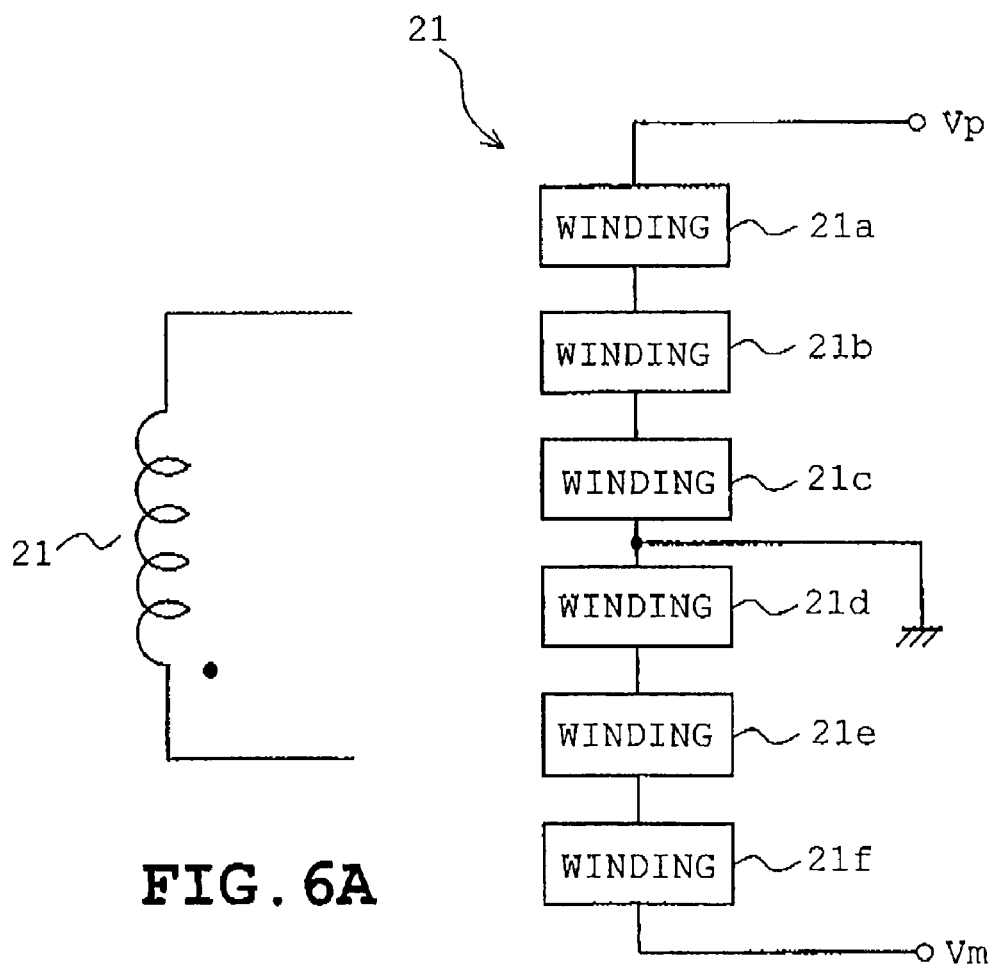
FIG. 6A
FIG. 6B

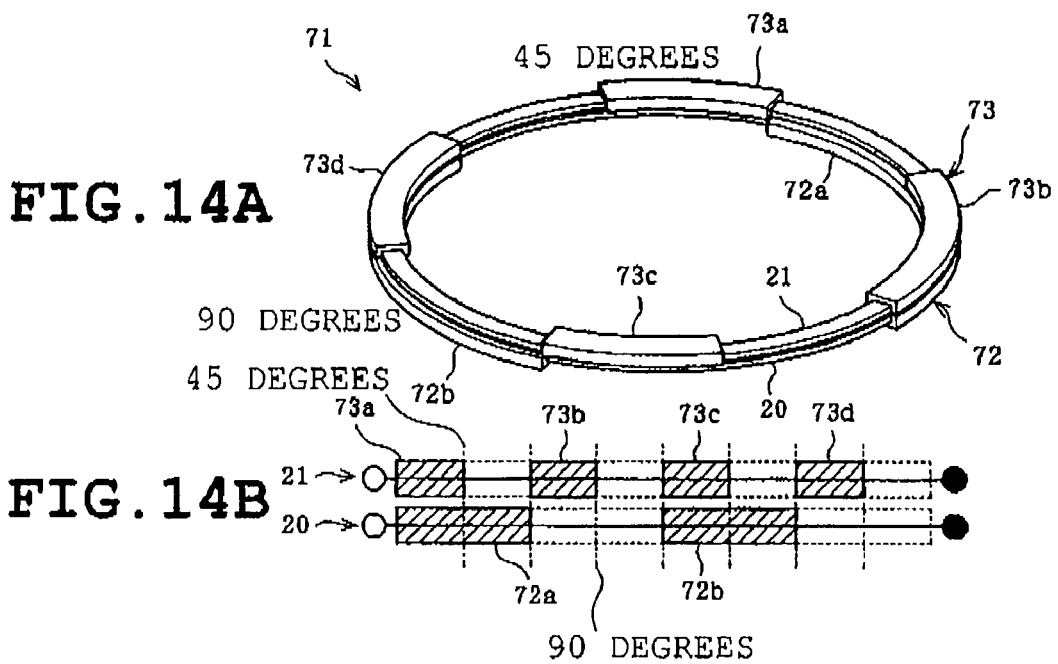
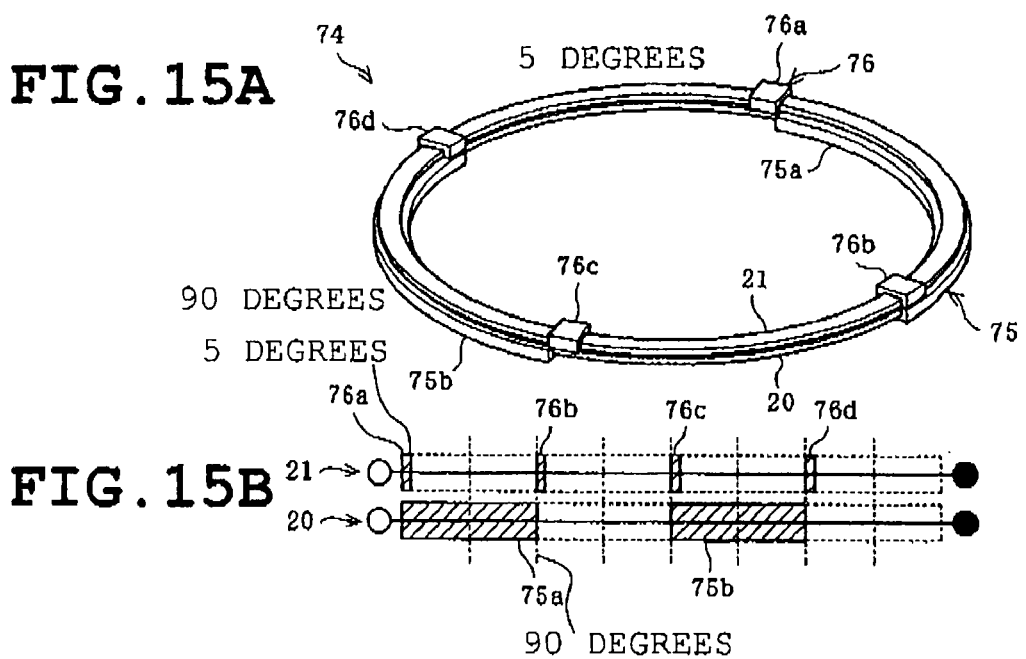
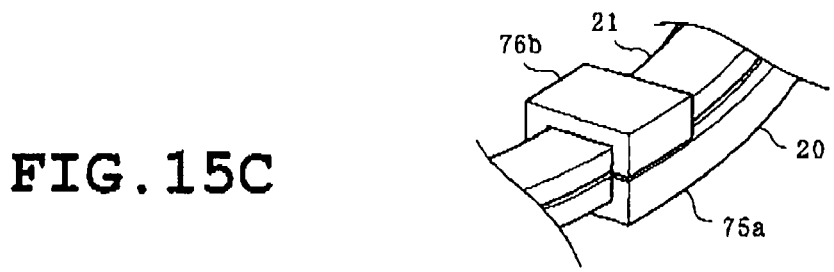

X-RAY CT DEVICE AND METHOD OF IMAGING USING THE SAME

CROSS-REFERENCE TO RELATED APPLICATIONS

This application is based upon and claims the benefit of priority from the prior Japanese Patent Application 2007-222722, filed on, Aug. 29, 2007 the entire contents of which are incorporated herein by reference.

FIELD

The present disclosure relates to an X-ray CT device provided with a stationary part and a rotary part configured rotatably relative to the stationary part. Power is supplied to an X-ray tube provided at the rotary part from the stationary part. The present disclosure also relates to a method of imaging with the X-ray CT device.

BACKGROUND

An X-ray CT (Computed Tomography) device is known for generating cross-sectional images of an object. More specifically, a cross-sectional image is generated by producing X-ray beams with an X-ray tube, which is passed through the object. The transmitted X-ray is converted into signals that provide basis for generating a cross-sectional image of the object. To produce such image, X-ray CT device is typically arranged to rotate a rotary part, including the X-ray tube and the X-ray detector, relative to a stationary part. Conventionally, in order to transmit power to the rotary part from the stationary part, a slip ring-brush configuration has been employed. However, the slip ring-brush configuration, requiring contact between the components, requires tedious maintenance work to recover component wear-out.

In view of the above concerns, JP 3827335 B discloses an electromagnetic induction transformer comprising a primary side and a secondary side, the primary side being provided at the stationary part and the secondary side being provided at the rotary part. The stationary part converts AC voltage provided by commercially available AC (Alternate Current) power into high-frequency voltage with a DC (Direct Current) power circuit and an inverter circuit. The high-frequency voltage is applied on the primary side. The rotary part, on the other hand, utilizes a high-voltage transformer for further stepping up the high-frequency voltage generated at the secondary side to a required voltage level to be supplied to the X-ray tube. The stepped up high-frequency voltage is rectified by the rectifier circuit, and the rectified DC voltage is applied to the X-ray tube. According to the above described configuration, burden of maintenance checkup for providing non-contact power transmission from the stationary part to the rotary part can be reduced.

The X-ray tube, however, requires application of high voltages ranging from 70 kV to 150 kV. The high-voltage transformer according to the conventional configuration needs to be increased in size in order to provide relatively higher voltages, which in turn leads to increased weight that may amount to 100 kg, for example. Such heavy and sizable high-voltage transformer, when provided at the rotary part, imparts increased centrifugal force upon rotation of the rotary part. Increased centrifugal force consequently requires structural reinforcement of the rotary part which in turn unwantedly causes increase in weight, leaving the problem of increased centrifugal force unsolved. Thus, one may conceive to reduce the maximum rotational speed in order to reduce the centrifugal force. However, maximum rotational speed of the rotary part is a critical factor in determining the quality of images generated by the X-ray CT device, such that when reduced, does not provide improved imaging quality.

Further, when heavy and sizable components are provided at the rotary part, balance of weight of the rotary part becomes unstabilized and may cause unwanted rotational variance. Rotational variance may be restrained by placing a balancer at the rotary part. However this will further increase the weight of the rotary part, which in turn increases the centrifugal force.

SUMMARY

The present disclosure provides an X-ray CT device that allows power to be supplied to an X-ray tube provided at a rotary part from a stationary part by non-contact power transmission. The present disclosure also provides a method of imaging using the X-ray CT device.

In one aspect, an X-ray CT device of the present disclosure includes a stationary part; a rotary part provided rotatably relative to the stationary part; an X-ray tube being provided at the rotary part and that radiates X-ray beams on an object of imaging; an X-ray detector being provided at the rotary part so as to oppose the X-ray tube, and that detects the X-ray beams passed through the object; an image processor that generates cross-sectional images of predetermined portions of the object based on a detection signal outputted from the X-ray detector; a display that shows the cross-sectional images based on output signals delivered from the image processor; a first transmitting section that is configured by a rotary step-up transformer having a primary winding residing at the stationary part and a secondary winding residing at the rotary part, and that steps up AC voltage provided by AC power source, and that further executes non-contact power transmission from the stationary part to the rotary part for supplying power to the X-ray tube.

In another aspect, an X-ray CT device of the present disclosure includes a stationary part; a rotary part provided rotatably relative to the stationary part; an X-ray tube being provided at the rotary part and that radiates X-ray beams on an object of imaging; an X-ray detector being provided at the rotary part so as to oppose the X-ray tube, and that detects X-ray beams passed through the object; an image processor that generates cross-sectional images of predetermined portions of the object based on a detection signal outputted from the X-ray detector; a display that shows the cross-sectional images based on output signals delivered from the image processor; a first transmitting section that is configured by a primary winding residing at the stationary part and a secondary winding residing at the rotary part, and that executes non-contact power transmission from the stationary part to the rotary part for supplying power to the X-ray tube; a second transmitting section being configured by a primary winding residing at the stationary part and a secondary winding residing at the rotary part, and that executes non-contact power transmission from the stationary part to the rotary part for supplying power to the X-ray detector, wherein the first transmitting section has a greater step-up ratio than the second transmitting section.

Yet, in another aspect, a method of imaging an object with an X-ray CT device includes a stationary part having a primary winding, a rotary part provided rotatably relative to the stationary part and having a secondary winding, a first transmitting section that is configured that steps up AC voltage provided by AC power source, and that further executes non-contact power transmission from the stationary part to the rotary part for supplying power to an X-ray tube provided at the rotary part that radiates X-ray beams, a second transmitting section that executes non-contact power transmission of power provided by AC power source to an X-ray detector provided on the rotary part for detecting X-ray beams passed through the object, an image processor that generates images of predetermined portions of the object based on a detection signal outputted from the X-ray detector, and a display that shows the generated images based on an output signal outputted from the image processor, the method including starting power supply to the second transmitting section; starting power supply to the first transmitting section and starting imaging of the object; stopping power supply to the first transmitting section and terminating imaging of the object; and stopping power supply to the second transmitting section.

According to the above described configuration, since AC voltage provided by AC power source need not be stepped up at the rotary part, heavy-weight components dedicated for voltage step-up need not be provided at the rotary part. Thus, non-contact power transmission can be executed from the stationary part to the rotary part for supplying power to the X-ray tube with lighter rotary part.

BRIEF DESCRIPTION OF THE DRAWINGS

Other objects, features and advantages of the present disclosure will become clear upon reviewing the following description of the exemplary embodiments with reference to the accompanying drawings, in which, FIG. 1 indicates an electric configuration of an X-ray CT device according to a first exemplary embodiment of the present disclosure;

FIG. 5 shows a detailed illustration of a winding provided at the step-up transformer;

FIG. 6A shows a circuit symbol of a secondary winding;

FIG. 6B is an equivalent of the secondary winding;

FIG. 14A corresponds to FIG. 9A and illustrates a fifth exemplary embodiment of the present disclosure;

FIG. 14B correspond to FIG. 10B.

FIG. 15A corresponds to FIG. 9A;

FIG. 15B corresponds to FIG. 9B; and

FIG. 15C is a partially exploded perspective view of the rotary step-up transformer.

DETAILED DESCRIPTION

A first exemplary embodiment of the present disclosure will be described with reference to FIGS. 1 to 7.

Figure 1:
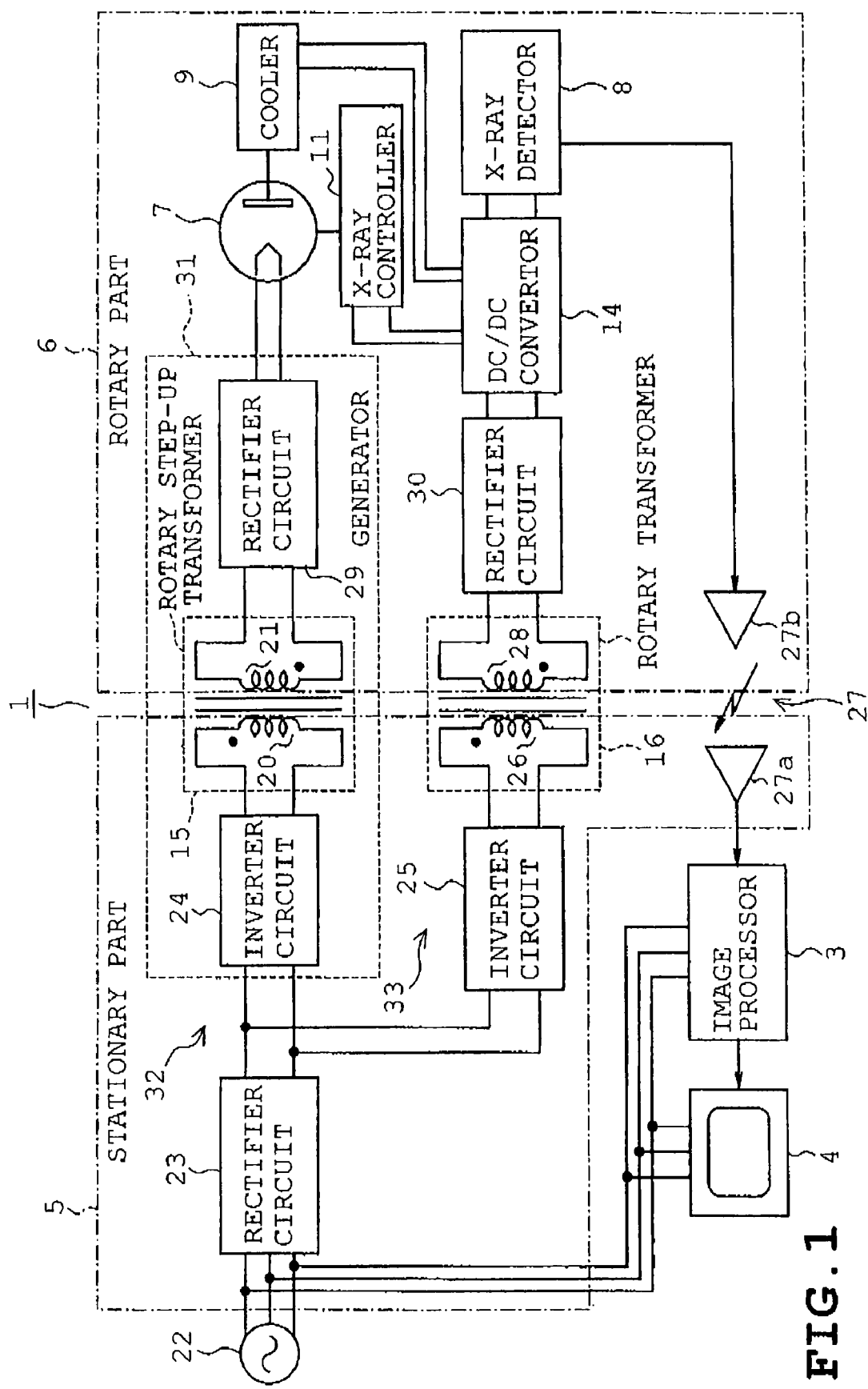
Figure 2:
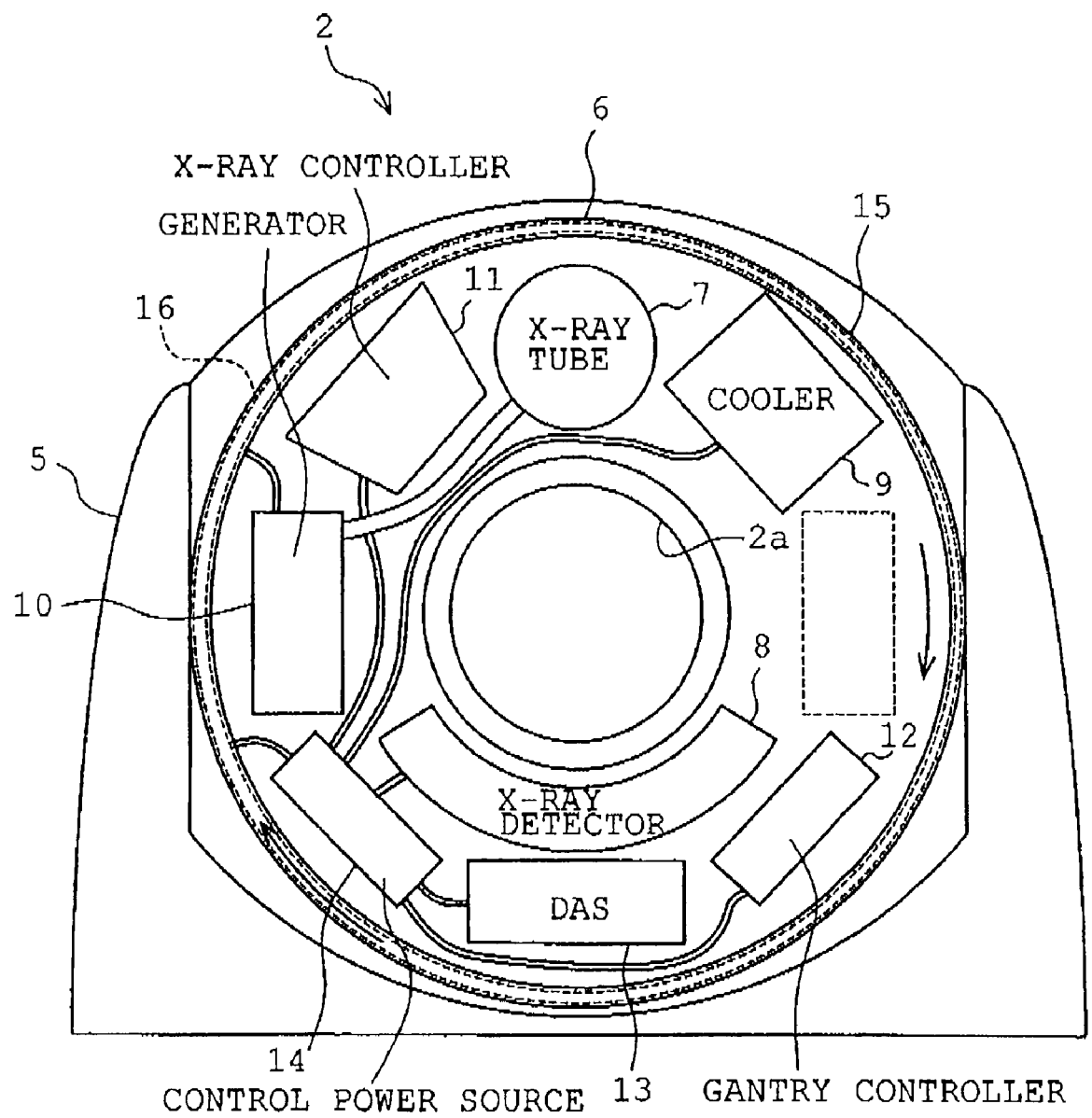
FIG. 2 is cross-sectional front view providing a look of a gantry and a part of its interior configuration.

Referring to FIGS. 1 and 2, an X-ray CT (computerized tomography) device 1 includes a gantry 2, an image processor 3, a display 4, and a bed (not shown). Gantry 2 radiates X-ray beams on an object from the periphery of the object. Gantry 2 also detects X-ray beams passed through the object. Image processor 3 generates cross-sectional image of the object based on the data detected from the transmitted X-ray beam. The generated cross-sectional image is shown on display 4. The bed receives and guides the object to gantry 2.

FIG. 2 is a cross-sectional front view depicting the exterior and schematic configuration of gantry 2 provided at X-ray CT device 1. As shown in FIG. 2, gantry 2 has an opening 2a formed as a cylindrical through hole defined substantially at its center. The bed carrying the object is passed through opening 2a to produce X-ray CT images. Gantry 2 comprises a stationary part 5 defining its exterior housing and a rotary part 6 rotatably supported by stationary part 5. Rotary part 6 rotates about opening 2a by a drive circuit and motor not shown.

Provided inside rotary part 6 are an X-ray tube 7 that produces X-ray beams and an X-ray detector 8 that detects X-ray beams passed through the object. X-ray tube 7 and X-ray detector 8 confront each other over opening 2a. X-ray detector 8 detects X-ray beams radiated from X-ray tube 7 and passed through the object. Further provided inside rotary part 6 are a cooler 9 for cooling X-ray tube 7, a generator 10 for supplying high voltage to X-ray tube 7, an X-ray controller 11, a gantry controller 12, a DAS 13, and a control power source 14. X-ray controller 11 controls output of X-ray tube 7 through control of generator 10 depending on preset settings.

X-ray controller 11 is capable of detecting abnormalities occurring at X-rat tube 7. When detecting such abnormalities, X-ray controller 11 stops power supply to X-ray tube 7. One exemplary approach for detecting abnormalities of X-ray tube 7 is a comparative approach in which actual amount of current and voltage provided to X-ray tube 7 is compared with a predetermined reference current and reference voltage. Gantry controller 12 controls components such as cooler 9 provided at rotary part 6. DAS (Data Acquisition System) 13 converts output (current signal) of X-ray detector 8 into digital data allowing processing with a computer. Control power source 14 supplies power to each component provided at rotary part 6 exclusive of X-ray tube 7.

Referring to FIG. 2, the area surrounded by a broken line indicates the portion where a heavy and sizable high-voltage transformer was conventionally provided. FIG. 2 merely schematically explains the availability of such space inside rotary part 6 of the present exemplary embodiment and does not precisely specify the positioning of each component thought it does properly indicate the relative positioning of X-ray tube 7 and X-ray detector 8. The components are positioned more elaborately in reality to balance the distribution of weight inside rotary part 6.

Rotary step-up transformer 15 and rotary transformer 16 being annular in form are provided to reside at both stationary part 5 and rotary part 6. Rotary step-up transformer 15 and rotary transformer 16 have a primary side and a secondary side respectively. The primary sides of rotary step-up transformer 15 and rotary transformer 16 are provided at stationary part 5 respectively whereas the secondary sides are provided at rotary part 6, respectively as will be described in detail afterwards. Power is supplied to X-ray tube 7 through rotary step-up transformer 15 and generator 10 provided at rotary part 6. Power is supplied to X-ray detector 8, cooler 9, X-ray controller 11, gantry controller 12, and DAS 13 through components such as rotary transformer 16 and control power source 14. Rotary step-up transformer 15 and rotary transformer 16 execute non-contact power transmission from stationary part 5 to rotary part 6.

Figure 3:
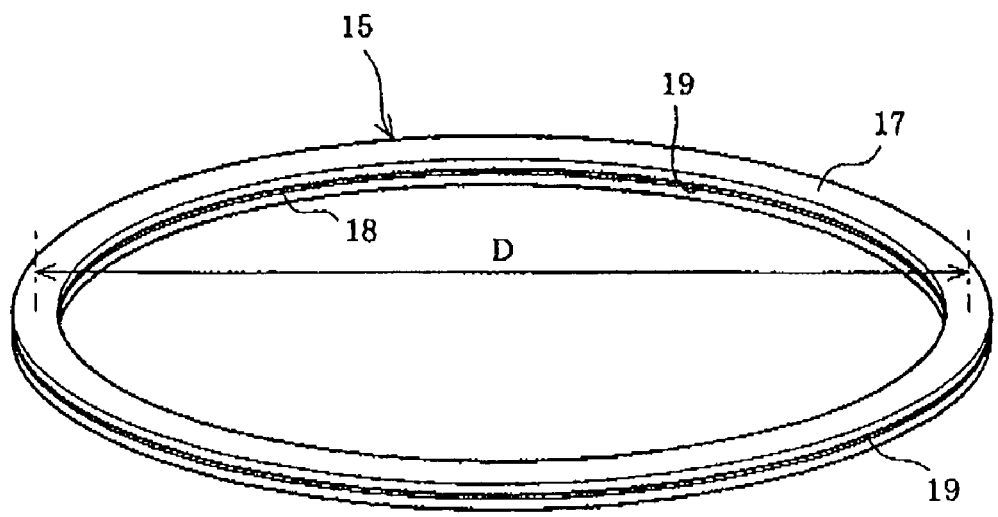
FIG. 3 is a schematic perspective view showing the entirety of a rotary step-up transformer.
Figure 4:
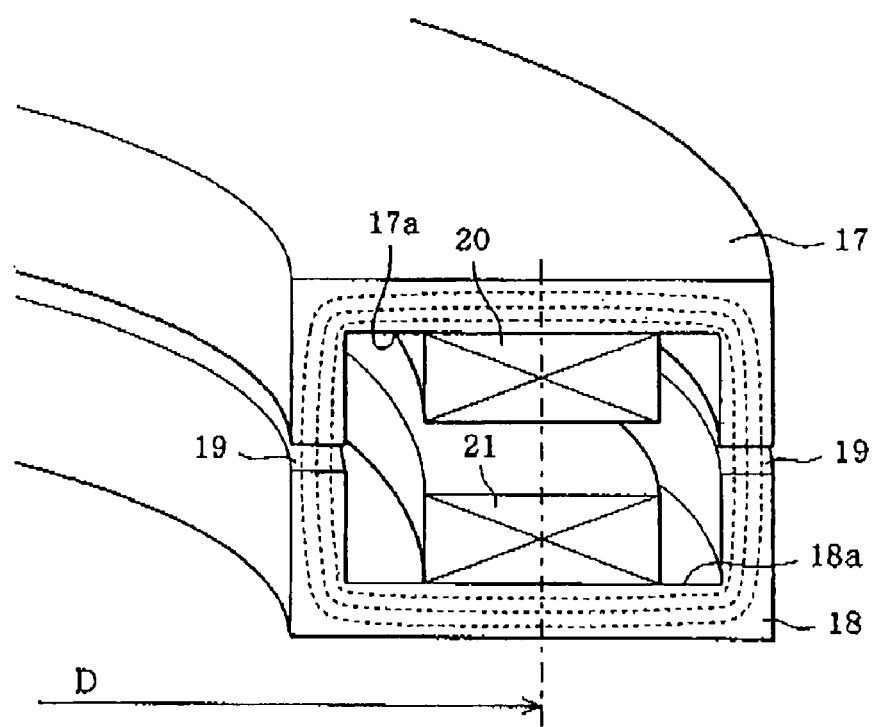
FIG. 4 is a circumferential cross-section of the rotary step-up transformer.

FIG. 3 is a schematic perspective view of rotary step-up transformer 15 and FIG. 4 provides an enlarged view of a circumferential cross-section of rotary step-up transformer 15. As can be seen in FIG. 3, rotary step-up transformer 15 is generally annular in form and is provided with a coaxial primary core 17 and a secondary core 18. Primary core 17 and secondary core 18 are made of magnetic materials such as magnetic steel and ferrite core. Primary core 17 is provided at stationary part 5 where as secondary core 18 is provided at rotary part 6, meaning that primary core 17 is fixed in place whereas secondary core 18 is rotatable about an axis.

Rotary step-up transformer 15 takes an axial-gap configuration where primary core 17 and secondary core 18 are axially disposed over a gap 19. Primary core 17 takes a reverse U-shape that is opened towards secondary core 18 or towards the bottom as viewed in FIG. 3. Primary core 17 is further provided with a circumferential groove 17a for securing a primary winding 20 via insulating material not shown.

Secondary core 18, on the other hand, has a U-shaped cross section that is opened towards the primary side as viewed in FIG. 3. Secondary core 18 is also provided with a circumferential groove 18a that has a secondary winding 21 wound on it. Primary and secondary cores 17 and 18 are designed to have constant thickness in the direction orthogonal to magnetic flux imparted to them. Gaps 19 between primary core 17 and secondary core 18 comprise air gaps which are configured at equal width throughout their circumference. In the present exemplary embodiment, primary core 17 and primary winding 20 reside in the primary side whereas secondary core 18 and secondary winding 21 reside in the secondary side. Rotary transformer 16 is similar in form to rotary step-up transformer 15 except for its insulative structure and winding configuration. The distinct insulative structure and winding configuration at rotary transformer 16 is designed to provide voltage transformation ratio of 1:1.

FIG. 1 is a block diagram indicating the electrical configuration of X-ray CT device 1. As can be seen in FIG. 1, stationary part 5 is provided with a rectifier circuit 23 that rectifies AC voltage supplied from AC power source 22, inverter circuits 24 and 25, primary winding 20 of rotary step-up transformer 15, primary winding 26 of rotary transformer 16, and a receiver 27a of a data transceiver 21. Rotary part 6, on the other hand, has secondary winding 21 of rotary step-up transformer 15, a secondary winding 28 of rotary transformer 16, rectifier circuits 29 and 30, X-ray tube 7, X-ray detector 8, cooler 9, control power source 14, and transmitter 27b of data transceiver 27. Inverter circuit 24, rotary step-up transformer 15, and rectifier circuit 29 described above constitute a generator 31. Generator 31 includes a generator 10 disposed at rotary part 6 as shown in FIG. 2, generator 10 comprising secondary side components of rotary step-up transformer 15 and rectifier circuit 29.

Turns ratio of primary winding 20 and secondary winding 21 of rotary step-up transformer 15 is set to provide a step-up ratio of "150" or greater. In other words, rotary step-up transformer 15 is configured so that voltage at the secondary side is at least 150 times greater than the primary side. Turns ratio of primary winding 26 and secondary winding 28 of rotary transformer 16 are is to provide a step-up ratio of "1". In other words, rotary transformer 16 is configured so that voltage at the secondary side and the primary side are identical. Step-up ratio of rotary transformer 16 may be configured at any given ratio other than "1" as long as it is below the step-up ratio of rotary step-up transformer 15.

AC power source 22 is a commercial AC power source which produces an output of 415 V (50 Hz/60 Hz) of three-phase. Rectifier circuit 23 is configured by diodes in three-phase bridge connection. Rectifier circuit 23 has an AC input terminal that is connected to an output terminal of AC power source 22. Rectifier circuit 23 further has a DC output terminal connected to input terminals of inverter circuits 24 and 25, respectively. Inverter circuits 24 and 25 convert DC voltage provided by rectifier circuit 23 into high-frequency voltage which is higher than the frequency (50 Hz/60 Hz) of commercial AC power source. High-frequency voltage outputted from inverter circuits 24 and 25 are applied to primary winding 20 of rotary step-up trans former 15 and winding 26 of rotary transformer 16, respectively.

In the present exemplary embodiment, rectifier circuit 23, inverter circuit 24 and rotary step-up transformer 15 constitute a first transmitting section 32. Rectifier circuit 23, inverter circuit 25, and rotary transformer 16 constitute a second transmitting section 33.

Data transceiver 27 performs non-contact data communication through medium such as light. Receiver 27a provided at stationary part 5 receives projection data transmitted from transmitter 27b provided at rotary part 6 to produce an output to image processor 3. Image processor 3 produces a cross-sectional view of the object based on the projection data provided by receiver 27a. Display 4 may comprise a liquid crystal display, for example, and receives input of data information representing cross-sectional images from image processor 3.

Image processor 3 and display 4 are each provided with a power source circuit (not shown) that converts three-phase AC voltage provided by AC power source 22 to their own operating voltages. Image processor 3 and display 4 operate with three-phase voltage supplied from AC power source 22. Power source may be supplied to image processor 3 and display 4 from external power source circuit.

Terminals at both ends of secondary winding 21 of rotary step-up transformer 15 are connected to AC input terminal of rectifier circuit 29. Rectifier circuit 29 is configured by bridge connected diodes. Rectifier circuit 29 rectifies high-frequency voltage generated at the terminals of secondary winding 21 to generate a DC voltage. DC voltage outputted from rectifier circuit 29 is applied to X-ray tube 7.

On the other hand, terminals at both ends of secondary winding 28 of rotary transformer 16 are connected to AC input terminal of rectifier circuit 30. Rectifier circuit 30 is configured by bridge connected diodes as in rectifier circuit 29. Rectifier circuit 30 has a DC output terminal connected to DC input terminal of control power source 14. Control power source 14 comprises a DC/DC converter that converts input DC voltage into the desired level of DC voltage. DC output of control power source 14 is provided to X-ray detector 8, cooler 9, and X-ray controller 11. Though not shown, DC output of control power source 14 is provided to gantry controller 12 and DAS 13.

X-ray detector 8 outputs a detection signal (current signal) that is inputted to DAS 13 (not shown in FIG. 1) and converted to digital data (projection data). DAS 13 transmits the projection data to receiver 27a at the stationary part 5 through transmitter 27b of data transceiver 27 by optical communication.

FIG. 5 is a cross-sectional view depicting the winding of rotary step-up transformer 15 in detail. As can be seen in FIG. 5, primary winding 20 comprises a litz wire, and secondary winding 21 comprises a litz wire or a flat copper line. Primary winding 20 is insulated from primary core 17 by micatape exhibiting high heat conductiveness. Secondary winding 21 is insulated from secondary core 18 by epoxy mold or hydraulic hardening. Secondary winding 21 and secondary core 18 are earthed. More specifically, supposing that secondary winding 21 has N number of turns, secondary winding 21 is earthed at (N×½)th turn.

FIGS. 6A and 6B schematically describe secondary winding 21. FIG. 6A symbolizes secondary winding 21 as represented in FIG. 1, and FIG. 6B indicates an equivalent circuit. It is assumed in FIG. 6B that secondary winding 21 has six turns. As can be seen in FIG. 6B, Secondary winding 21 has windings 21a to 21f provided between terminal Vp and terminal Vm. Windings 21a to 21f represent each of the six turns of secondary winding 21.

For instance, if 9 kV of voltage is generated between the terminals of secondary winding 21 with terminal Vm being earthed, voltage level at terminal Vp indicates +9 kV and terminal Vm indicates 0V. The level of voltage generated at each of windings 21a to 21f is a quotient of inter-terminal voltage (9 kV) divided by number of turns (6), thus, amounting to 1.5V. As a result, there could be a high potential difference ranging from 6 kV to 9 kV between the earthed secondary core 18 and windings 21a to 21c residing relatively closer to terminal Vp and having relatively higher potential.

Contrastingly, if the intermediate portion is earthed as described in FIGS. 5 and 6A and 6B of the present exemplary embodiment, and voltage level of 9 kV is similarly generated between the terminals of secondary winding 21, terminal Vp indicates a voltage level of +4.5 kV whereas terminal Vm indicates a voltage level of −4.5 kV. In this case, the difference in potential between secondary core 18 and windings 21a to 21c having relatively higher potential amounts to 4.5 kV at maximum at terminal Vp. Likewise, the difference in potential between secondary core 18 and windings 21d to 21f having relatively lower potential (located relatively closer to terminal Vm) amounts to 4.5 kV at maximum at terminal Vm. This means that potential difference between secondary winding 21 and secondary core 18 can be reduced by earthing the intermediary portion of secondary winding 21.

The above described configuration provides the following operation and effect.

Three phase AC voltage (415V) supplied from AC power source 22 is rectified by rectifier circuit 23 to produce a DC output which in turn is converted into high-frequency voltage by inverter circuit 24. The high-frequency voltage outputted from inverter circuit 24 is applied to primary winding 20 of rotary step-up transformer 15 to generate a high-frequency current flow which generates magnetic flux indicated by broken line in FIG. 4. The magnetic flux transmits power to the secondary side, consequently generating a high-frequency voltage between the terminals of the secondary winding 21 which is at least 150 times greater than the high-frequency voltage applied between the terminals of primary winding 20. The high-frequency voltage generated between the terminals of the secondary winding 21 is rectified by rectifier circuit 29.

DC voltage outputted from rectifier circuit 29 is applied to X-ray tube 7. The level of voltage required to radiate X-ray from X-ray tube 7 is approximately 70 kV to 150 kV, though it may vary depending upon the type X-ray tube 7 (See General Requirements for High-voltage Generators of Medical X-ray Apparatus: JIS Z 4702). Thus, step-up ratio of rotary step-up transformer 15 is set to output 70 kV of DC voltage, the lowermost limit of the above described range, from rectifier circuit 29.

Maximum level of AC voltage of AC power source 22 is $415V \times \sqrt{2} \approx 587V$. The ratio of the aforementioned lowermost limit 70 kV and the highest level of AC voltage described above is 120. However, considering the voltage drop occurring at rectifier circuit 23, inverter circuit 24, rotary step-up transformer 15 and rectifier circuit 29, rotary step-up transformer 15 requires step-up ratio setting of at least "150". The above described settings of step-up ratio for rotary step-up transformer 15 allows voltage ranging from 70 kV to 150 kV to be applied on X-ray tube 7 for radiation of X-ray beams.

DC output from rectifier circuit 23 is supplied to inverter circuit 25 as well. When high-frequency voltage outputted from inverter circuit 25 is applied on primary winding 26 of rotary trance 16 to cause high-frequency current to flow, magnetic flux is generated as was the case for rotary step-up transformer 15. The magnetic flux transmits power to the secondary side to generate a high-frequency voltage between the terminals of secondary winding 28 that equals the voltage level generated at primary winding 26. The high-frequency voltage generated between the terminals of secondary winding 28 is rectified by rectifier circuit 30. DC voltage outputted from rectifier circuit 30 is converted into DC voltage of desired voltage level by control power source 14 and thereafter supplied to components such as X-ray detector 8 and cooler 9.

Figure 7:
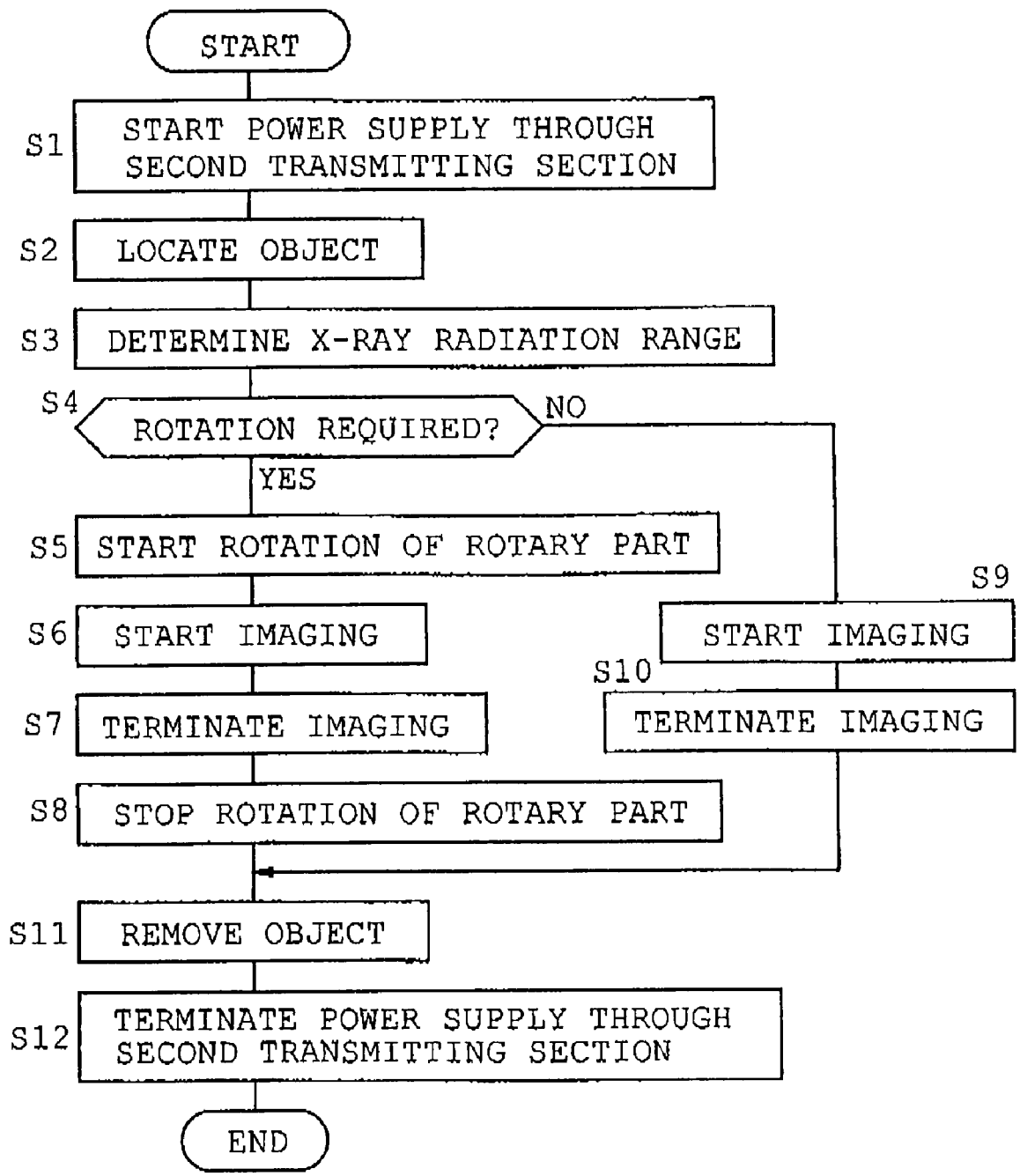
FIG. 7 shows a sequence of an imaging process executed by the X-ray CT device.

Next, a description will be given on a method of generating images with X-ray CT device 1 with reference to FIG. 7.

First, inverter circuit 25 is driven to supply power provided by AC power source 22 to rotary part 6 through rectifier circuit 23, inverter circuit 25, and rotary transformer 16, which in turn activates control power source 14. The output produced by control power source 14 activates X-ray detector 8, cooler 9, X-ray controller 11, gantry controller 12, and DAS 13 (step S1). Then, after placing the object of imaging on gantry 2, required position information is transmitted to gantry controller 12 to position the object relative to the X-ray radiator (step S2).

After positioning the object, range of X-ray beam to be radiated on object placed on gantry 2 is determined (step S3). After determining the radiation range, a selection is made whether or not to rotate rotary part 6 (step S4). If rotation is required ("Yes" decision is made at step S4), rotation of rotary part 6 is started (step S5) and control proceeds to step S6.

At step S6, inverter circuit 24 is driven to supply power provided by AC power source 22 to rotary part 6 through rectifier circuit 23, inverter circuit 24, and rotary transformer 15, which in turn starts imaging of the object. That is, when power is supplied to the rotary part 6, stepped up voltage is applied on X-ray tube 7 to radiate X-ray beams on the object. The X-ray beams passed through the object is inputted to X-ray detector 8. X-ray detector 8 converts the X-ray beam passed through the object into data representing the targeted portion of the object and forwards the converted data to image processor 3. Based on the forwarded data, image processor 3 generates a cross-sectional image of the targeted portion of the object and forwards the generated image to display 4. Display 4 shows the cross-sectional image for user's view.

At step S6, the detection signal delivered from X-ray detector 8 may be forwarded to image processor 3 as available while X-ray beam radiation from X-ray tube 7 is ongoing. Alternatively, data of the targeted portion may be accumulated at X-ray detector 8 and accumulated data may be forwarded to image processor 3 in a batch after X-ray beam radiation and rotary part 6 rotation has been completed.

Imaging is terminated at the moment when the generated cross-sectional image is shown on display 4, at which point drive of inverter circuit 24 is stopped, and power supply through rotary step-up transformer 15 is stopped (step S7). After completing imaging, rotation of rotary part 6 is stopped (step S8).

When imaging of the object is executed without rotation of rotary part 6, (when "No" decision is made at step S4), step 39 and S10 are executed instead of steps S6 and S7. Steps S9 and 10 pertaining to operations performed at image processor 3 and display 4 differs from steps 36 and S7 in that at step S9, image processor 3 forwards a two-dimensional image data, representing the targeted portion of the object, to display 4 based on the forwarded data. Display 4 shows the forwarded two-dimensional image. At step S10, imaging is terminated the moment the two-dimensional data is shown on display 4.

After rotation is stopped at step S8, or imaging is terminated at step S10, object is removed from gantry 2 (step S11). Then, by stopping the drive of inverter circuit 25, power supply through rotary transformer 16 is stopped to terminate imaging (step S12).

In case imaging of the object needs to be executed consecutively, the process may return to step S2 from step S11 and repeat steps S2 to S11. When positioning the object at step S2, power may be supplied to X-ray tube 7 through rotary step-up transformer 15 to radiate X-ray beams for scano imaging. Scano imaging allows accurate positioning of X-ray beam radiation and also retrieves maximum amount of exposure to radiation for each portion of the object to allow the X-ray beam radiation to be optimized.

As described above, non-contact transmission of power to rotary part 6 from stationary part 5 eliminates maintenance for component wear-out, which was formerly required in contact transmission, thereby improving system reliability. Non contact transmission also contributes to noise-reduction which reduces stress suffered by the patient when the device is used in medical applications. Further, since a heavy-weight high-voltage transformer no longer needs to be provided at rotary part 6, rotary part 6 can be reduced in size and weight, which in turn reduces the centrifugal force upon rotation of rotary part 6. The reduction of centrifugal force allows increase in maximum rotation speed, which improves the quality of the generated image. Weight reduction of rotary part 6 contributes to reduction of electricity consumption for rotation of rotary part 6.

Further, two transmitting sections have been provided for power supply from stationary part 5 to rotary part 6. The first transmitting section supplies power to X-ray tube 7 through rotary step-up transformer 15, whereas the second transmitting section supplies power to other components provided at rotary part 6 such as X-ray detector 8 and cooler 9 through rotary transformer 16. Thus, power is supplied constantly to control systems such as X-ray detector 8, cooler 9, and X-ray controller 11, and power supply may be turned ON/OFF for X-ray tube 7 alone, Such configuration allows further reduction in electricity consumption of X-ray CT device 1. Further, even if an abnormal error occurs in the first transmitting section, steady power supplied to X-ray controller 11 through the second transmitting section allows abnormal behavior of X-ray tube 7 to be detected by X-ray controller 11 so that operation may be stopped to provide safe and reliable emergency operation. In case of emergency, since steady power is supplied to cooler 9 through the second transmitting section, X-ray tube 7 can be cooled on a constant basis to provide reliable operation of the system.

As can be seen in FIG. 2, space enclosed by broken line is available inside rotary part 6. This space may be utilized to provide an additional set of X-ray tube and X-ray detector to reduce the duration of imaging process as well as improve the quality of the generated image.

Yet, further secondary winding 21 of rotary step-up transformer 15 has been earthed at the intermediate portion (N×½th turn) of to reduce potential difference between secondary winding 21 and the earthed secondary core 18. Such configuration allows the length of insulation provided on the secondary side bearing high level of voltage to be reduced. This consequently reduces the distance between the primary and the secondary windings, which in turn reduces primary current. Furthermore, smaller spacing for winding allows a compact and low cost system.

A description will be given hereinafter on a second exemplary embodiment of the present disclosure with reference to FIG. 8.

Figure 8:
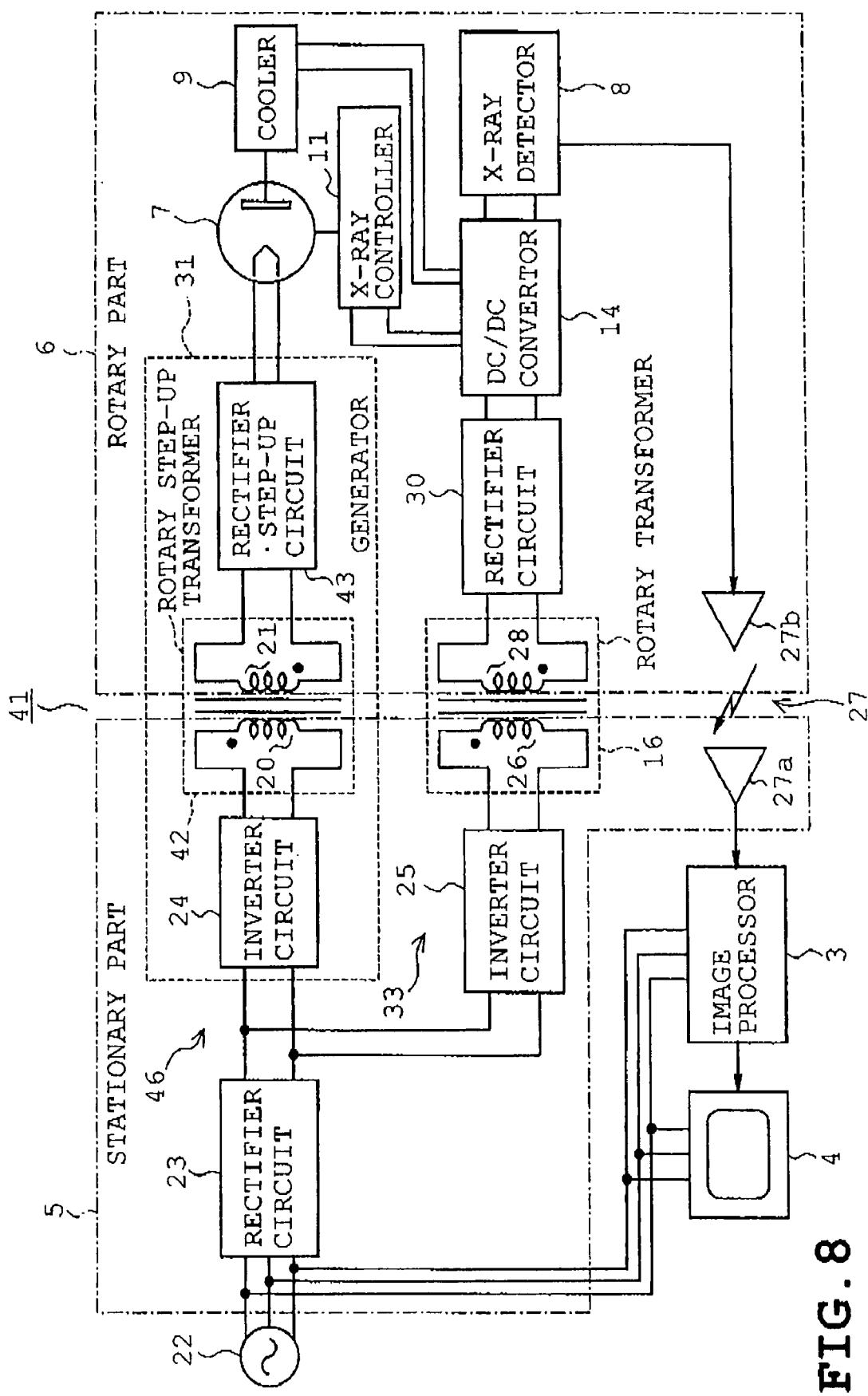
FIG. 8 corresponds to FIG. 1 and illustrates a second exemplary embodiment of the present disclosure.

FIG. 8 corresponds to FIG. 1 of the first exemplary embodiment. Elements that are identical to the first exemplary embodiment are represented by identical reference symbols without detailed descriptions. Description will be given hereinafter on portions that differ. Referring to FIG. 8, X-ray CT device 41 differs from X-ray CT device 1 in that rotary step-up transformer 15 is replaced by rotary step-up transformer 42 and that rectifier circuit 29 is replaced by rectifier/step up circuit 43.

Rotary step-up transformer 42 is similar in structure to rotary step-up transformer 15, however has a different step-up ratio. Rotary step-up transformer 42 has the turns ratio of primary winding 44 and secondary winding 45 is set so that step-up ratio amounts to "7" or greater. Rectifier/step up circuit 43 (corresponding to voltage step up element) comprises a multiplex Cockcroft-Walton circuit and is configured by passive components such as diodes and capacitors. In the second exemplary embodiment, first transmitting section 46 comprises rectifier circuit 23, inverter circuit 24, rotary step-up transformer 42, and rectifier/step up circuit 43.

In the present exemplary embodiment, the high-frequency voltage generated between the terminals of secondary winding 45 of rotary step-up transformer 42 is rectified and stepped up by rectifier/step up circuit, and the stepped up voltage is applied on X-ray tube 7. As described earlier, X-ray tube 7 ultimately requires application of DC voltage ranging from approximately 70 kV to 150 kV. Thus, in the present embodiment, voltage is stepped up to approximately 120 kV by combined use of rotary step-up transformer 42 and rectifier/step up circuit 43.

When "extra high voltage" (above 7000V in AC voltage) is generated at the secondary side of rotary step up-transfer 42, insulative structure at the secondary side becomes complex. Thus, step-up ratio is set within the range of "high voltage" greater than 600V but equal to or less than 7000V. The nominal voltage normally used within the aforementioned range of "high voltage" is 3300V and 6600V; however, it is desirable to arrange the voltage level to 3000V which is below the halfway point of the high voltage range. The ratio of voltage level 3000V required as secondary voltage and the maximum AC voltage 587V of AC power source is approximately "5". However, considering the voltage drop at rectifier circuit 23, inverter circuit 24, and rotary step-up transformer 42, step-up ratio of rotary step-up transformer 42 needs to be set at "7" or greater. Rectifier/step up circuit 43 needs to be configured to allow the secondary voltage (approximately 3000V) of rotary step-up transformer 42 to be stepped up to DC voltage of approximately 120 kV.

As described above, the effects of the first exemplary embodiment can be achieved even when DC voltage for radiating X-ray beams on X-ray tube 7 is stepped up in two steps by rotary step-up transformer 42 and rectifier/step up circuit provided at rotary part 6. Since step-up ratio has been set so that the voltage level at the secondary side of rotary step-up transformer 42 amounts to 3000V within the range of "high voltage", the insulative configuration at the secondary side can be simplified compared to when "extra high voltage" exceeding 7000V is generated at the secondary side, for example.

Since rectifier/step up circuit 43 is configured by passive elements, the attempt to increase the step-up ratio results in increase in the number of parts used. Thus, the step-up ratio of rectifier/step up circuit 43 has been restrained at a minimum ratio that would allow the voltage level of the secondary side of rotary step-up transformer 42 to be stepped up to the required voltage level to be supplied to X-ray tube 7. Thus, by keeping the number of parts used for rectifier/step up circuit 43 minimum, rectifier/step up circuit 43, and consequently rotary part 6 can be reduced in weight.

Next, a description will be given on a third exemplary embodiment of the present disclosure with reference to FIG. 9.

Figure 9:
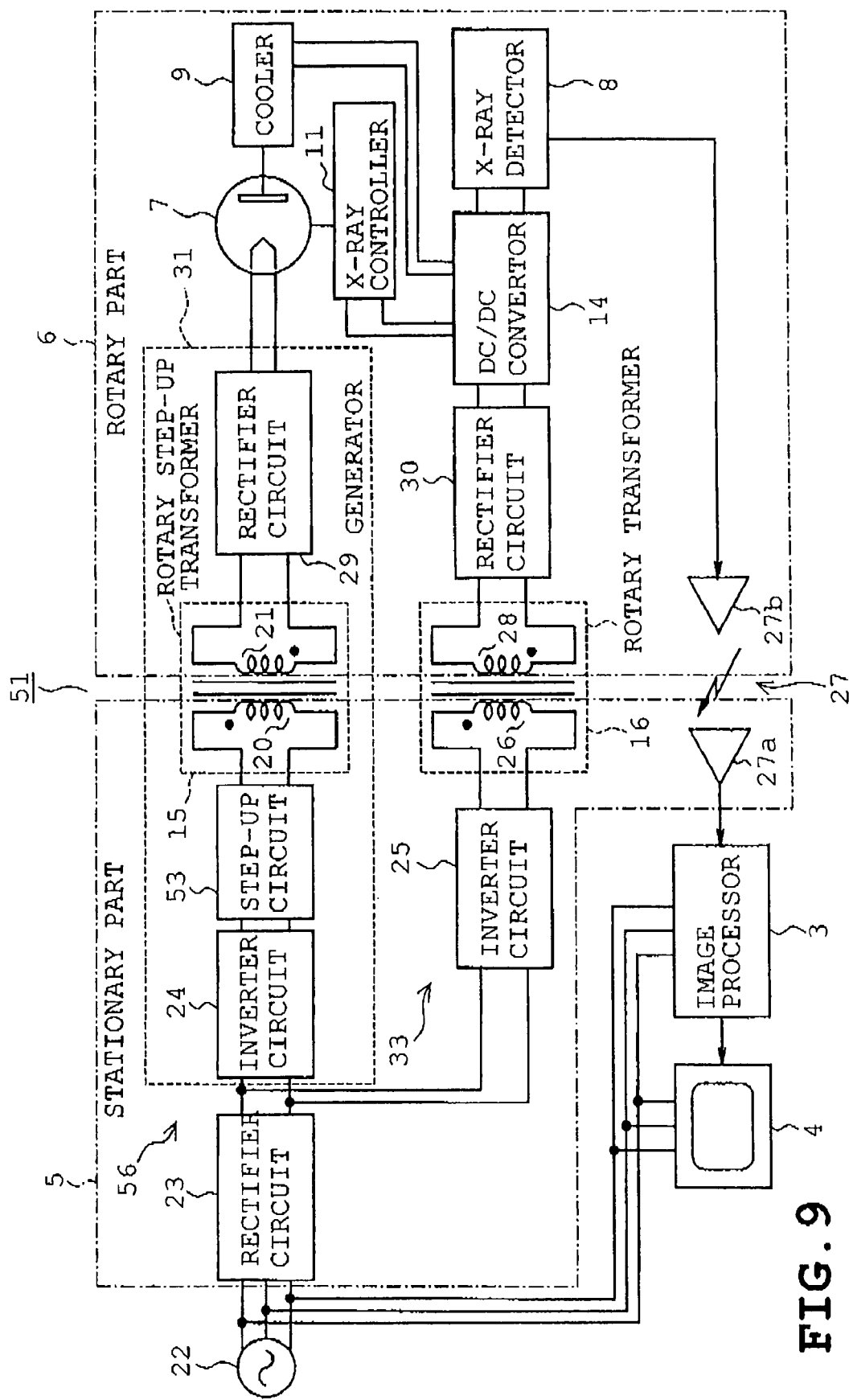
FIG. 9 corresponds to FIG. 1 and illustrates a third exemplary embodiment of the present disclosure.

FIG. 9 corresponds to FIG. 1 of the first exemplary embodiment. Elements that are identical to the first exemplary embodiment are represented by identical reference symbols without detailed descriptions. Description will be given hereinafter on portions that differ. Referring to FIG. 9, X-ray CT device 51 differs from X-ray CT device 1 in that rotary step-up transformer 15 is replaced by rotary step-up transformer 52 and that step up circuit 53 is added to stationary part 5.

Rotary step-up transformer 52 is similar in structure to rotary step-up transformer 15, however has a different step-up ratio. Rotary step-up transformer 52 has the turns ratio of primary winding 54 and secondary winding 55 set so that step-up ratio amounts to "10" or greater. Step-up circuit 53 (corresponding to step-up element) comprises a step-up transformer, for example. In the third exemplary embodiment, a first transmitting section 56 comprises rectifier circuit 23, inverter circuit 24, step-up circuit 53, and rotary step-up transformer 52.

Step-up transformer 53 steps up the high-frequency voltage outputted from inverter circuit 24 and applies the stepped up voltage on primary winding 20 of rotary step-up transformer 52. Thus in the present exemplary embodiment, voltage is stepped up to the required voltage level (70 kV to 150 kV) to be supplied to X-ray tube 7 by combined use of step-up circuit 53 and rotary step-up transformer 52.

As described earlier, insulative structure at the secondary side of rotary step-up transformer 52 becomes complex as the voltage level at the winding is increased. In the present exemplary embodiment, voltage generated between the terminals of secondary winding 55 of rotary step-up transformer 52 is rectified by rectifier circuit 29 and thereafter supplied to X-ray tube 7. Thus, voltage generated between the terminals of secondary winding 55 needs to be exceptionally high so that it can be supplied to X-ray tube 7. Step-up ratio is thus set so that voltage between the terminals of primary winding 54 is at or less 7 kV which falls within the high voltage range (above 600V but equal to or less 7000V). Thus, step-up ratio of rotary step-up transformer 52 is set at "10" or greater. Step up circuit 53 needs to be configured to allow the maximum AC voltage level 587V of AC power source 22 to be stepped up to DC voltage of approximately 7 kV. Voltage level at the primary side of rotary step-up transformer 52 is thus, arranged at 7 kV or less (within the range of high voltage), to allow the insulative structure of the primary side to be simplified.

As described above, the effects of the first exemplary embodiment can be achieved even when DC voltage for radiating X-ray beams on X-ray tube 7 is stepped up in two steps by step up circuit 53 and rotary step-up transformer 52. Further, since step up circuit 53 is placed in stationary part 5, rotary part 6 can be further reduced in weight.

Next, a description will be given hereinafter on a fourth exemplary embodiment with reference to FIGS. 10A to 13.

Figure 10A:
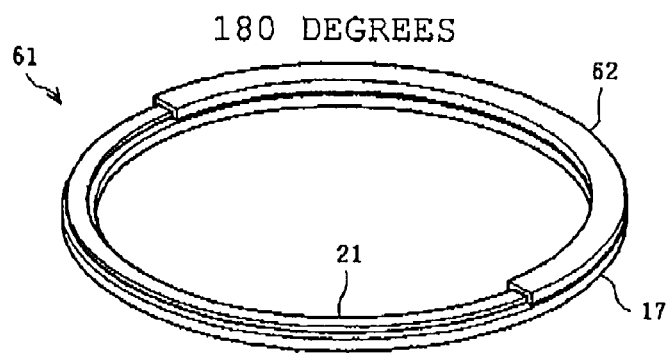
FIG. 10A corresponds to FIG. 3 and illustrates a fourth exemplary embodiment of the present disclosure.
Figure 10B:
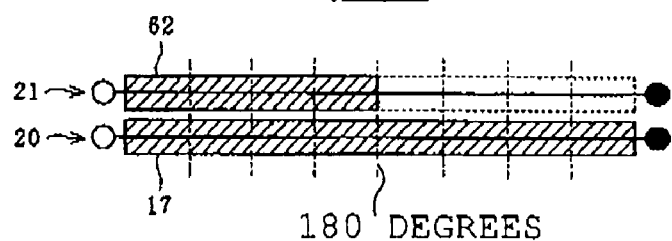
FIG. 10B shows positioning of cores relative to winding.
Figure 11A:
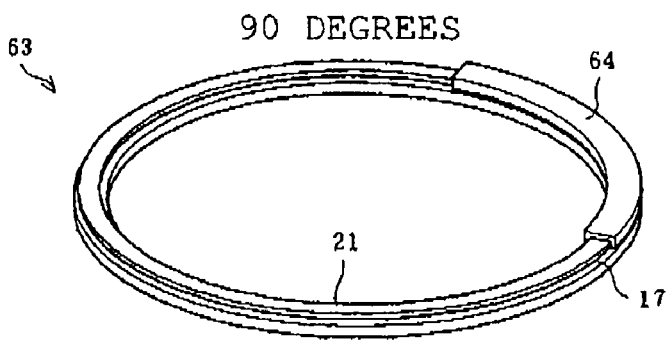
FIG. 11A corresponds to FIG. 9A.
Figure 11B:
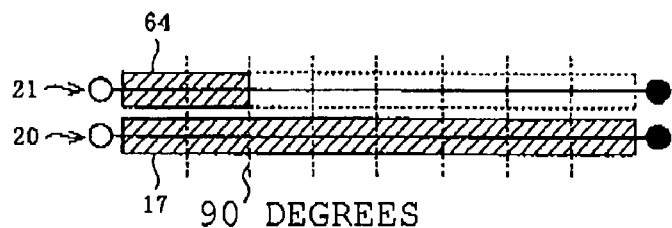
FIG. 11B corresponds to FIG. 9B.
Figure 12A:
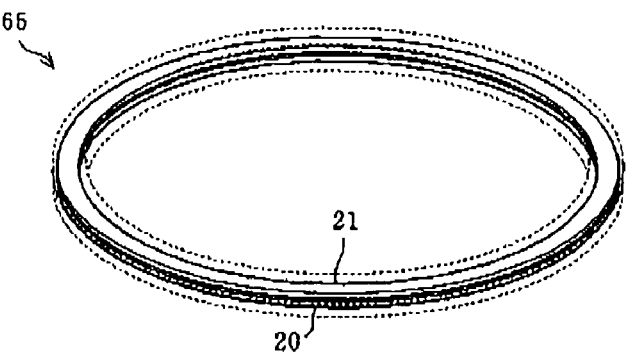
FIG. 12A corresponds to FIG. 9A.
Figure 12B:
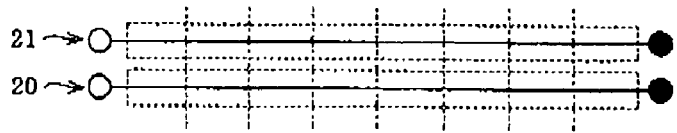
FIG. 12B corresponds to FIG. 9B.

The present exemplary embodiment provides a modified example of the shape of the secondary core described in the first exemplary embodiment. FIGS. 10A, 11A, and 12A correspond to FIG. 3 illustrating the first exemplary embodiment, and elements that are identical to the first exemplary embodiment are represented by identical reference symbols without detailed descriptions. FIGS. 10B, 11B, and 12B show positioning of the core relative to the winding. In FIGS. 10B, 11B, and 12B, white circle (○) indicates the start of winding and black circle (●) indicates the end of winding. The hatched portion surrounding the winding indicates the core. It is to be noted that secondary core is shown on the upper side in FIGS. 10A to 12B.

Referring to FIG. 10A, rotary step-up transformer 61 includes an annular primary core 17 and an arc-shaped secondary core 62 having a central angle of 180 degrees. As can be seen in FIG. 10B, the central angle of the area where primary core 17 and secondary core 62 confront each other (hereinafter referred to as confronting angle) is 180 degrees. Referring now to FIG. 11A, rotary step-up transformer 63 includes an annular primary core and a secondary core 64 having a central angle of 90 degrees. As can be seen in FIG. 11B, primary core 17 and secondary core 64 of rotary step-up transformer 63 has a confronting angle of 90 degrees. In the present exemplary embodiment, secondary core 62 and secondary winding 21, and secondary core 64 and secondary winding 21 each correspond to the secondary side.

Figure 13:
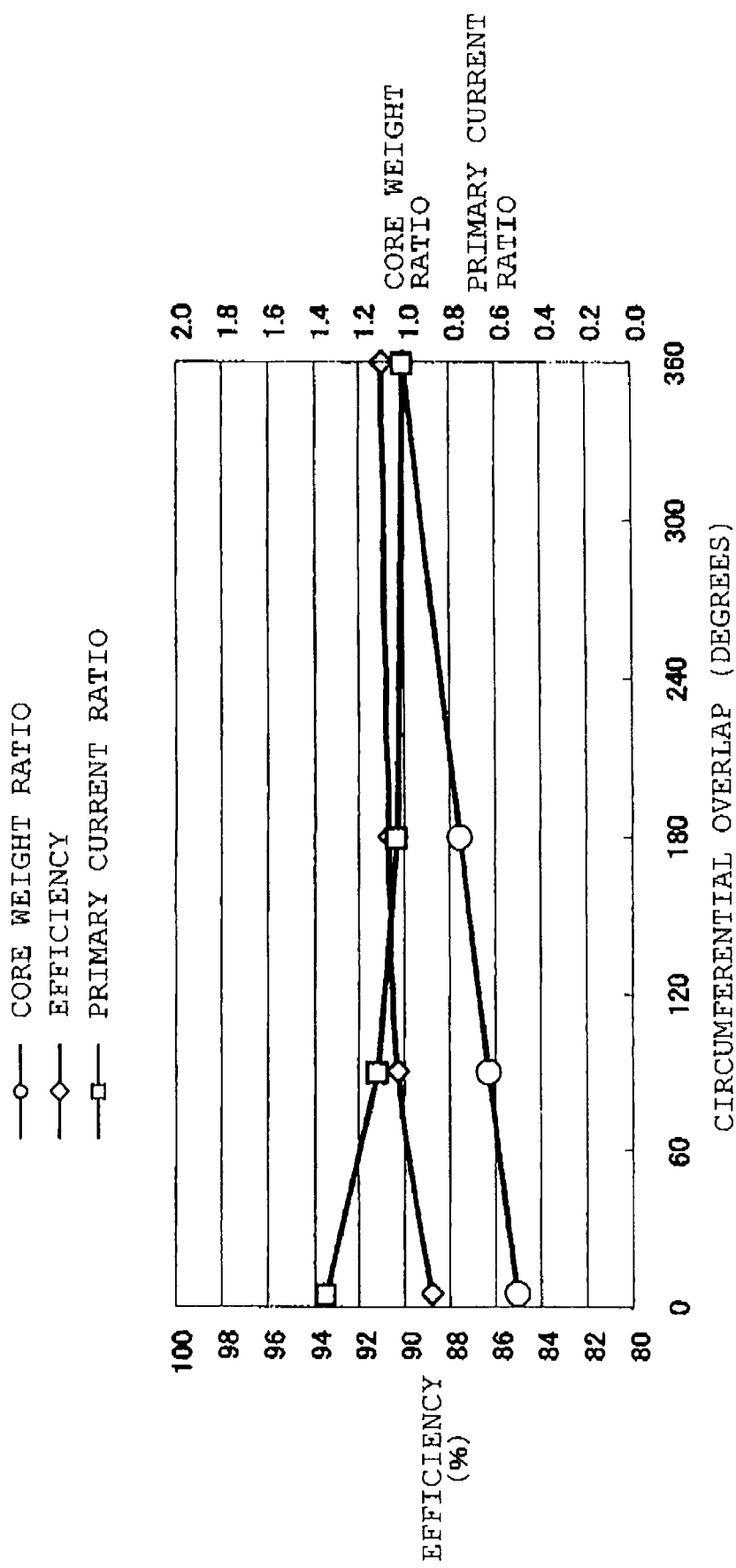
FIG. 13 indicates a confronting angle of cores, efficiency, weight ratio, and primary current ratio.

FIG. 13 indicates the relation between confronting angle of primary and secondary cores, efficiency of rotary step-up transformer, weight ratio, and primary current ratio. Core weight ratio and primary current ratio indicate relative relation to rotary step-up transformer 15 (having confronting angle of primary core and secondary core of 360 degrees) which is represented by 1. In this case, efficiency of rotary step-up transformer 15 is approximately 91%, for example.

According to the configuration having (confronting angle=180 degrees indicated in FIGS. 10A and 10B, efficiency is slightly lowered and primary current ratio is slightly increased; however, core weight ratio is extensively reduced (weight ratio=0.75). On the other hand, according to the configuration having confronting angle=90 degrees shown in FIGS. 11A and 11B, efficiency is similarly slightly lowered and primary current ratio is slightly increased; however, core weight ratio is extensively reduced (weight ratio=0.625). To summarize, as the confronting angle between the primary core and secondary core are decreased, core weight ratio is considerably reduced at the expense of consequent increase in leak current that reduces efficiency and increases the primary current.

The use of rotary step-up transformer 61 or 63 of the present exemplary embodiment allows the weight ratio of the core (the secondary core, in this case) to be reduced while maintaining the level of efficiency and primary current ratio achieved in the first exemplary embodiment. As a result, weight of rotary part 6 can be further reduced while achieving the operation and effect of the first exemplary embodiment. Weight reduction of rotary part 6 further allows quality improvement of the generated image and reduction of electricity consumption. Further, the secondary core can be made with less amount of material (such as magnetic steel or ferrite core) consumption to reduce manufacturing cost.

It the decrease of efficiency of the rotary step-up transformer and increase of primary current is within a permissible range, the secondary core may be further reduced in size to a central angle between 180 degrees to 90 degrees or even less than 90 degrees. In other words, the only requirement is that the central angle of the arc-shaped core is 180 degrees or less. Further, as can be seen in rotary step-up transformer 65 of FIGS. 12A and 12B, either of the primary or the secondary core may be eliminated. Yet, further, the secondary core may comprise two arcs each having a central angle of 90 degrees, for example, or three arcs each having a central angle of 30 degrees, for example. In other words, the secondary core may comprise a plurality of arc-shaped cores that amount to a total central angle of 180 degrees or less.

Next, a fifth exemplary embodiment will be described with reference to FIGS. 14A to 15C.

The present exemplary embodiment describes modified examples of the primary and secondary cores described in the first to third exemplary embodiments. FIGS. 14A and 15A correspond to FIG. 10A of the fourth exemplary embodiment, and FIGS. 14B and 15B correspond to FIG. 10B. FIG. 15C is a partially exploded perspective view of the rotary step-up transformer.

Referring to FIG. 14A, rotary step-up transformer 71 comprises a primary core 72 composed of two cores 72*a* and 72*b* formed as 90 degree-arcs, and a secondary core 73 composed of four cores 73*a* to 73*d* formed as 45 degree-arcs. As can be seen in FIG. 14B, cores 72*a* and 72*b* are disposed at 180 degree interval (equally spaced) and cores 73*a* to 73*d* are disposed at 90 degree intervals (equally spaced). Primary core 72 and secondary core 73 define a confronting angle of 90 degrees. That is, total confronting angle between cores 72*a* and 72*b* and cores 73*a* to 73*d* amount to 90 degrees regardless of the rotational position of secondary core 73.

Referring to FIG. 15A, rotary step-up transformer 74 comprises a primary core 75 composed of two cores 75*a* and 75*b* formed as 90 degree-arcs, and a secondary core 76 composed of four cores 76*a* to 76*d* formed as 5-degree arcs. As can be seen in FIG. 15B, cores 75*a* and 75*b* are disposed at 180 degree interval (equally spaced) and cores 76*a* to 76*d* are disposed at 90 degree intervals (equally spaced). As can be seen in FIGS. 15B and 15C, primary core 75 and secondary core 76 define a confronting angle of 10 degrees. That is, total confronting angle between cores 75*a* and 75*b* and cores 76*a* to 76*d* amount to 10 degrees regardless of the rotational position of secondary core 76. In the present exemplary embodiment, primary core 72 and primary winding 20, and primary core 75 and primary winding 20 correspond to the primary side, whereas secondary core 73 and secondary winding 21 and secondary core 76 and secondary winding 21 corresponding to the secondary side.

The use of rotary step-up transformer 71 allows the weight ratio of the core to be reduced while maintaining the level of efficiency and primary current ratio achieved in the configuration (having confronting angle of 90 degrees) indicated in FIGS. 11A and 11B of the fourth exemplary embodiment. The use of rotary step-up transformer 74 further allows the weight ratio of the core to be further reduced while maintaining the level of efficiency and primary current ratio achieved in the configuration (not shown) having a confronting angle of 10 degrees in the fourth exemplary embodiment.

According to the present exemplary embodiment, material consumption of materials such as magnetic steel and ferrite core at the cores can be reduced while achieving the operation and effect of the first exemplary embodiment to provide reduced manufacturing cost. Furthermore, since cores 73*a* to 73*d* (76*a* to 76*d*) of secondary core 73 and 76 have been disposed at constant angular interval of 90 degrees, the weight of rotary part 6 is better balanced. The above described configuration prevents rotational variance of rotary part 6.

Angle θ1 of the arcs comprising each core and the number of cores represented by n provided in the primary core is not limited to the above described configuration but may take any given value that meets the following formula.

$$\theta 1 = 180/n \text{[degrees]} \tag{1}$$

Angle θ2 of the arcs comprising each core in the secondary core is not limited to the above described configuration but may be any given value that meets the following formula.

$$\theta 2 < \theta 1 \text{ [degrees]} \tag{2}$$

The present disclosure is not limited to the above described and illustrated exemplary embodiments but may be modified or expanded as follows.

Power transmission from stationary part 5 to rotary part 6 need not be rendered by two transmitting sections. In other words, rotary transformer 16, inverter circuit 25 and rectifier circuit 30 are not required. In such case, power supplied from stationary part 5 to rotary part 6 through rotary step-up transformer 15 may be stepped-down by a power source circuit, or the like, and provided to components such as a cooler provided at rotary part 6.

In case sufficient length of insulation can be provided at the secondary side of the rotary step-up transformer, the secondary winding need not be earthed at the intermediate winding turn.

In the fourth exemplary embodiment, if the weight of rotary part 6 has been sufficiently reduced, the configuration of the primary core and the secondary core may be reversed. In other words, the secondary core may be annular in form and the primary core may be formed as arcs having central angle of 180 degrees or less.

The foregoing description and drawings are merely illustrative of the principles of the present disclosure and are not to be construed in a limited sense. Various changes and modifications will become apparent to those of ordinary skill in the art. All such changes and modifications are seen to fall within the scope of the disclosure as defined by the appended claims.

What is claimed is:

1. An X-ray CT device, comprising:
    a stationary part;
    a rotary part provided rotatably relative to the stationary part;
    an X-ray tube being provided at the rotary part and that radiates X-ray beams on an object of imaging;
    an X-ray detector being provided at the rotary part so as to oppose the X-ray tube, and that detects the X-ray beams passed through the object;
    an image processor that generates cross-sectional images of predetermined portions of the object based on a detection signal outputted from the X-ray detector;
    a display that shows the cross-sectional images based on output signals delivered from the image processor;
    a first transmitting section that is configured by a rotary step-up transformer having a primary winding residing at the stationary part and a secondary winding residing at the rotary part, and that steps up AC voltage provided by AC power source, and that further executes non-contact power transmission from the stationary part to the rotary part for supplying power to the X-ray tube.

2. The X-ray CT device according to claim 1, further comprising a second transmitting section being configured by a rotary transformer having a primary winding residing at the stationary part and a secondary winding residing at the rotary part, and that executes non-contact power transmission of AC voltage provided by AC power source from the stationary part to the rotary part.

3. The X-ray CT device according to claim 2, wherein power is transmitted to the X-ray detector through the second transmitting section.

4. The X-ray CT device according to claim 2, wherein the rotary part includes a cooler that cools the X-ray tube, the cooler being provided with power through the second transmitting section.

5. The X-ray CT device according to claim 2, wherein the rotary part includes an X-ray controller that controls operation of the X-ray tube, the X-ray controller being provided with power through the second transmitting section.

6. The X-ray CT device according to claim 1, wherein plurality sets of the X-ray tube and the X-ray detectors are provided.

7. The X-ray CT device according to claim 1, wherein the first transmitting section includes a rectifier circuit being provided at the stationary part and that coverts AC voltage provided from the AC power source into DC voltage, and an inverter circuit being provided at the stationary part and that converts the DC voltage converted by the rectifier circuit into high-frequency voltage being higher in frequency than the AC voltage, and that applies the high-frequency voltage on the primary winding of the rotary step-up transformer.

8. The X-ray CT device according to claim 1, wherein the first transmitting section includes a rectifier circuit being provided at the stationary part and that coverts AC voltage provided from the AC power source into DC voltage, an inverter circuit being provided at the stationary part and that converts the DC voltage converted by the rectifier circuit into high-frequency voltage being higher in frequency than the AC voltage, and that applies the high-frequency voltage on the primary winding of the rotary step-up transformer, and a step-up element being provided at the rotary part and including a diode and a capacitor, the step-up element rectifying and stepping up the high-frequency voltage generated at the secondary winding of the rotary step-up transformer, the step-up element further supplying the stepped up high-frequency voltage to the X-ray tube.

9. The X-ray CT device according to claim 1, wherein the first transmitting section includes a rectifier circuit being provided at the stationary part and that coverts AC voltage provided from the AC power source into DC voltage, an inverter circuit being provided at the stationary part, and that converts the DC voltage converted by the rectifier circuit into high-frequency voltage being higher in frequency than the AC voltage, and a step-up element being provided at the stationary part, the step-up element stepping up the high-frequency voltage outputted from the inverter circuit and applying the stepped up high-frequency voltage on the primary winding of the rotary step-up transformer.

10. The X-ray CT device according to claim 1, wherein the rotary step-up transformer includes an annular primary side residing at the stationary part, a primary winding being wound on the primary side, a secondary side residing at the rotary part and being disposed to confront the primary side over a gap, and a secondary winding being wound on the secondary side.

11. The X-ray CT device according to claim 10, wherein one of the primary side or the secondary side is either provided with a core along its entire circumference or no core at all, whereas other is provided with at least one arc-shaped core that has a central angle amounting to 180 degrees or less.

12. The X-ray CT device according to claim 10, wherein either of the primary side or the secondary side is provided with n number of arc-shaped cores having a central angle $\theta_1$ given by $\theta_1 = 180/n$, n being an integer equal to or greater than 1, and the cores being spaced at constant angular intervals, whereas other is provided with 2 times n number of arc-shaped cores having a central angle $\theta_2$ less than the central angle $\theta_1$, the secondary cores being spaced at constant angular intervals.

13. The X-ray CT device according to claim 10, wherein the secondary winding has N number of turns, the secondary winding being earthed at an intermediate portion located at N/2th turn.

14. An X-ray CT device, comprising:
a stationary part;
a rotary part provided rotatably relative to the stationary part;
an X-ray tube being provided at the rotary part and that radiates X-ray beams on an object of imaging;
an X-ray detector being provided at the rotary part so as to oppose the X-ray tube, and that detects X-ray beams passed through the object;
an image processor that generates cross-sectional images of predetermined portions of the object based on a detection signal outputted from the X-ray detector;
a display that shows the cross-sectional images based on output signals delivered from the image processor;
a first transmitting section that is configured by a primary winding residing at the stationary part and a secondary winding residing at the rotary part, and that executes non-contact power transmission from the stationary part to the rotary part for supplying power to the X-ray tube;
a second transmitting section being configured by a primary winding residing at the stationary part and a secondary winding residing at the rotary part, and that executes non-contact power transmission from the stationary part to the rotary part for supplying power to the X-ray detector,
wherein the first transmitting section has a greater step-up ratio than the second transmitting section.

15. The X-ray CT device according to claim 14, wherein the rotary part includes a cooler that cools the X-ray tube, the cooler being provided with power through the second transmitting section.

16. The X-ray CT device according to claim 14, wherein the rotary part includes an X-ray controller that controls operation of the X-ray tube, the X-ray controller and the X-ray detector being provided with power through the second transmitting section.

17. The X-ray CT device according to claim 14, wherein plurality sets of the X-ray tube and the X-ray detectors are provided.

18. A method of imaging an object with an X-ray CT device including a stationary part having a primary winding, a rotary part provided rotatably relative to the stationary part and having a secondary winding, a first transmitting section that is configured that steps up AC voltage provided by AC power source, and that further executes non-contact power transmission from the stationary part to the rotary part for supplying power to an X-ray tube provided at the rotary part that radiates X-ray beams, a second transmitting section that executes non-contact power transmission of power provided by AC power source to an X-ray detector provided on the rotary part for detecting X-ray beams passed through the object, an image processor that generates images of predetermined portions of the object based on a detection signal outputted from the X-ray detector, and a display that shows the generated images based on an output signal outputted from the image processor, the method comprising:
- starting power supply to the second transmitting section;
- starting power supply to the first transmitting section and starting imaging of the object;
- stopping power supply to the first transmitting section and terminating imaging of the object; and
- stopping power supply to the second transmitting section.

19. The method according to claim 18, further comprising starting rotation of the rotary part prior to starting power supply to the first transmitting section and starting imaging of the object, and further comprising stopping rotation of the rotary part after stopping power supply to the first transmitting section and terminating imaging of the object.

* * * * *